US011878014B2

(12) United States Patent
Pollard et al.

(10) Patent No.: US 11,878,014 B2
(45) Date of Patent: *Jan. 23, 2024

(54) KETAMINE OR DEXTROMETHORPHAN FORMULATIONS AND METHODS OF USE

(71) Applicant: West Virginia University, Morgantown, WV (US)

(72) Inventors: Scott Pollard, Cody, WY (US); Patrick Marshalek, Morgantown, WV (US); Rae Matsumoto, Stockton, CA (US)

(73) Assignee: West Virginia University, Morgantown, WV (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/449,196

(22) Filed: Sep. 28, 2021

(65) Prior Publication Data

US 2022/0008412 A1    Jan. 13, 2022

Related U.S. Application Data

(63) Continuation of application No. 14/644,608, filed on Mar. 11, 2015, now Pat. No. 11,207,316.

(Continued)

(51) Int. Cl.
*A61K 31/485* (2006.01)
*A61K 31/135* (2006.01)

(52) U.S. Cl.
CPC .......... *A61K 31/485* (2013.01); *A61K 31/135* (2013.01)

(58) Field of Classification Search
CPC ............................. A61K 31/485; A61K 31/135
See application file for complete search history.

(56) References Cited

U.S. PATENT DOCUMENTS

| 5,232,950 A | 8/1993 | Marcoux |
| 6,197,830 B1 | 3/2001 | Frome |

(Continued)

FOREIGN PATENT DOCUMENTS

AU    2012238330 B1    4/2013

OTHER PUBLICATIONS

Krishnarajah, J., iX Biopharma Ltd., 2019, B18, biopharmadealmakers.nature.com.

(Continued)

*Primary Examiner* — Savitha M Rao
*Assistant Examiner* — Andrew P Lee
(74) *Attorney, Agent, or Firm* — Buchanan Ingersoll & Rooney PC; Craig G. Cochenour

(57) ABSTRACT

The present invention provides a method of treating depression disease in a treatment resistant patient comprising administering to a mucosal membrane of a patient an effective amount of a pharmaceutically acceptable composition comprising an effective amount of ketamine or dextromethorphan, wherein the mucosal administration of the ketamine or dextromethorphan containing composition allows for the mucosal absorption of the composition eliminating the digestive tract of the patient for effecting a rapid acting antidepressant treatment of the treatment resistant patient. This method includes administering the composition to a patient's mucosal membrane of a respiratory tract, a genitourinary tract, an oral tract, or rectal tract of the patient. A pharmaceutically acceptable composition comprising ketamine or dextromethorphan and a vehicle is disclosed. A biomarker for identifying a depressive disease is set forth.

10 Claims, 1 Drawing Sheet

Related U.S. Application Data

(60) Provisional application No. 62/005,326, filed on May 30, 2014.

(56) References Cited

U.S. PATENT DOCUMENTS

| | | |
|---|---|---|
| 8,268,866 B2 | 9/2012 | Guitton et al. |
| 8,785,500 B2 | 7/2014 | Charney et al. |
| 2007/0287753 A1 | 12/2007 | Charney et al. |
| 2011/0178177 A1* | 7/2011 | Wolicki ............... A61K 31/18 514/561 |
| 2012/0225949 A1* | 9/2012 | Papalos ............... A61P 25/18 514/646 |

OTHER PUBLICATIONS

Rolan, P. et al., The absolute bioavailability of racemic ketamine from a novel sublingual formulation, British Journal of Clinical Pharmacology, 2013, 1011-1016 77:6, The British Pharmacological Society.

* cited by examiner

Methods

- 17 patients with major depressive disorder who were identified as treatment resistant, underwent treatment with low, sub-anesthetic dose ketamine (0.5 mg / kg) transbucally/sublingually at the Chestnut Ridge Center in Morgantown, WV. This single dose of ketamine lasts for up to two weeks.
- Patients were instructed to place liquid ketamine in their mouth and to retain it for as long as possible, mimicking a transbucal/sublingual route.
- A retrospective chart review was performed to measure ketamine use and efficacy, patient demographics, concurrent medications to ketamine, reported ketamine side effects, and ketamine refill history. Efficacy was based upon chart entries regarding mood improvement/affect, length of ketamine, and refill history.

Results

Patient Demographics

Age

| ≤20 | 20-39 | 40-59 | ≥60 |
|---|---|---|---|
| 0% | 29% | 53% | 17% |

Gender

| Male | Female |
|---|---|
| 12% | 88% |

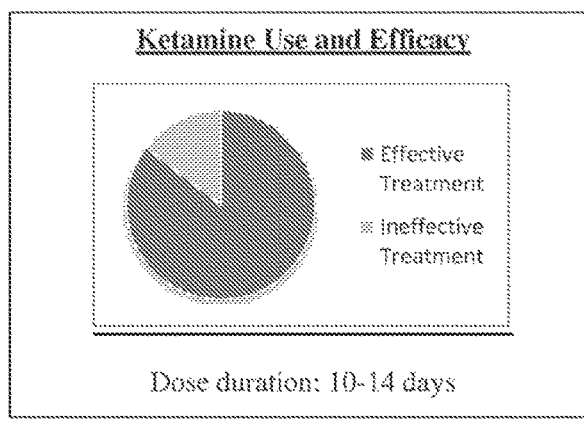

Ketamine Use and Efficacy

- Effective Treatment
- Ineffective Treatment

Dose duration: 10-14 days

Concurrent Medications

| | |
|---|---|
| SNRI | 65% |
| Stimulant | 47% |
| Folate replacement | 41% |
| Benzodiazepines | 41% |
| SSRI | 29% |
| Antipsychotics | 29% |
| Antihistamine (hydroxyzine) | 29% |
| Beta blocker | 18% |
| Neuropathic pain (Lyrica®) | 18% |
| TCA | 18% |

Drug Interactions / Adverse Effects

| | |
|---|---|
| Klonopin, Ativan, Lyrica, Pamelor, Atarax, Doxepin, Trazodone | CNS Depression |
| Haldol, Remeron | Additive/ CNS Effects |
| Inderal, Cardura, Prazosin | Hypotension |
| Vyvanse, Adderal | Cardiac Effects |

Side Effects reported
Light headache (n=1)   slight dizziness (n=1)

KETAMINE OR DEXTROMETHORPHAN FORMULATIONS AND METHODS OF USE

CROSS-REFERENCE TO RELATED APPLICATION

This utility patent application claims the benefit of U.S. patent application Ser. No. 14/644,608, filed on Mar. 11, 2015, now U.S. Pat. No. 11,207,316, granted Dec. 28, 2021, which claims the benefit of U.S. Provisional Patent Application Ser. No. 62/005,326, filed on May 30, 2014. The entire contents of U.S. patent application Ser. No. 14/644,608 and U.S. Provisional Patent Application Ser. No. 62/005,326 are incorporated by reference into this utility patent application as if fully written herein.

BACKGROUND OF THE INVENTION

1. Field of the Invention

The present invention provides for the mucosal, and preferably buccal formulations of compositions containing ketamine or dextromethorphan and methods of administering mucosal and buccal formulations of compositions containing ketamine or dextromethorphan for treatment of unipolar and bipolar depression and depression disease that is resistant to treatment.

2. Description of the Background Art

Depression affects about 20% of the population and it is the leading cause of disability in the U.S. Current treatments for depression are inadequate. It takes several weeks of treatment before beneficial effects are observed, and about 30% of individuals still do not respond. There is thus a pressing need to identify effective and fast acting therapeutic options for individuals suffering from depression. Accumulating evidence indicates that the anesthetic ketamine can produce rapid antidepressant effects that last for up to two weeks. Use of this option, however, is severely limited because intravenous administration of ketamine must be done in an inpatient setting, and is accompanied by notable side effects. The identification of a fast acting antidepressant drug that can be used in a general clinical population would represent a transformative advance in psychiatry.

Depression affects about 20% of Americans. It now begins earlier in life than in past decades, and rates are increasing. Individuals with depression have a higher risk for a variety of health problems including substance abuse, eating disorders, heart disease, and stroke. It is the leading cause of disability in the U.S., costing approximately $44 billion in loss of productivity in a given year. Despite advances in antidepressant therapy, it still takes four to six weeks before approved medications are effective which results in significant morbidity. Further, about 30% of patients do not respond to treatment. Given that depression is one of the most common and costly brain diseases, there is an urgent need to develop more effective medications to treat this devastating disorder. Historical antidepressant drugs: Antidepressant drugs were discovered serendipitously in the 1950s, with the repurposing of a monoamine oxidase inhibitor (iproniazid) and tricyclic (imipramine) that were originally approved for other indications. The introduction of selective serotonin reuptake inhibitors (SSRIs) followed in the late 1980s, which greatly improved the side effect profile of antidepressant therapy, but did not provide significant advances in terms of efficacy or onset of action. These limitations are concerning because drugs that are the mainstay of antidepressant pharmacotherapy have a delayed onset of action (2-4 weeks) during which time patients are at high risk for suicide. Fast acting antidepressant drugs: A major breakthrough in the treatment of depression came in 2000 with ketamine reported as a fast acting antidepressant drug. Ketamine is a noncompetitive NMDA glutamate receptor antagonist that has been used as an intravenous anesthetic agent for several decades and has been shown to have rapid acting antidepressant effects in as fast as two hours in sub-anesthetic doses. Intravenous ketamine is almost exclusively used in the inpatient setting and is known for serious adverse effects such as hallucinations and sedation, but the widespread use of ketamine remains limited by its side effect profile which includes perceptual disturbances, confusion, and a short lived "high". The present invention provides a long felt and unresolved and unmet need for clinical methods and transbuccal formulations of ketamine or dextromethorphan for treating depression in patients.

SUMMARY OF THE INVENTION

The present method provides a method of treating depressive disease (depression) in a patient comprising administering to a mucosal membrane of a patient an effective amount of a composition comprising an effective amount of ketamine or dextromethorphan, or both ketamine and dextromethorphan, wherein said mucosal administration of said composition allows for the transmucosal absorption of the composition into the patient's blood stream thereby eliminating the digestive tract of said patient for providing a rapid acting antidepressant effect for treating depression in the patient. Preferably, this method of includes administering said composition to said mucosal membrane of said patient over a time period from one millisecond to ten minutes, and more preferably this method includes wherein the time period of administration ranges from one second to three minutes. This method includes wherein said composition is contained within a dosage form capable of being administered to the mucosa of said patient or to the mucosal membrane of said patient. Preferably, this method includes wherein said dosage form is a liquid, gel, powder. More preferably, this method includes wherein said dosage form is in the form of a pharmaceutically acceptable troche, film, capsule, tablet, particle, solution, suspension, lollipop, lozenge, emulsion, spray, or aerosol. More preferably, this method includes wherein said effective amount of said ketamine is 0.5 mg per kilogram of a patient's body mass. In a most preferred embodiment of this invention, the method, as described herein, includes administering said composition to said mucosal membrane that is in an oral cavity of said patient. The oral cavity is preferably the buccal cavity of the patient. The methods of this invention include wherein the depression is selected from the group of unipolar depression disease, bipolar depression disease, and depression treatment resistant disease.

Another embodiment of this invention provides a pharmaceutically acceptable composition comprising an effective amount of ketamine or dextromethorphan, or both ketamine and dextromethorphan, wherein said ketamine or said dextromethorphan is distributed within a pharmaceutically acceptable vehicle, wherein said vehicle is capable of being placed in contact with a mucosal membrane of a patient. The composition and said vehicle are capable of delivery to an oral cavity of said patient, and more preferably are capable of delivery to a buccal cavity of the oral cavity of said patient. The pharmaceutically acceptable composition of this invention includes a dosage form that is a liquid, gel, or powder. Further, the pharmaceutically acceptable composition has a dosage form of a pharmaceutically acceptable troche, film, capsule, tablet, particle, solution, suspension, lollipop, lozenge, emulsion, spray, or aerosol. Preferably, the effective amount of said ketamine in said composition is 0.5 mg per kilogram of a patient's body mass.

In another embodiment of this invention, a pharmaceutically acceptable composition is provided comprising an effective amount of ketamine or dextromethorphan, or both ketamine and dextromethorphan, wherein said ketamine or said dextromethorphan is distributed within a pharmaceutically acceptable vehicle, wherein said vehicle is capable of being placed in contact with a mucosal membrane of a patient. The composition and said vehicle are capable of delivery to an oral cavity of said patient, and more preferably are capable of delivery to a buccal cavity of the oral cavity of said patient, and wherein the pharmaceutically acceptable vehicle is a device having a mucoadhesive layer containing said ketamine buffered to a pH of between about 4.0 and 7.0, and a non-adhesive backing layer buffered to a pH of between 4.0 and 6.0 wherein the pH of the mucoadhesive layer and the pH of the non-adhesive backing layer are different, wherein the mucoadhesive layer and the non-adhesive backing layer comprise different combinations of polymers but each layer comprises at least one water-erodible polymer selected from the group of cellulosic polymers, olefinic polymers, polyethers, and polyalcohols. The water-erodible polymer is at least one selected from the group consisting of polyacrylic acid, sodium carboxymethylcellulose, hydroxyethyl cellulose, hydroxyethylmethyl cellulose, hydroxyethyl cellulose, hydroxypropyl cellulose, polyvinyl alcohol, polyethylene glycol, polyethylene oxide, and ethylene oxide-propylene oxide co-polymers. Preferably, the pharmaceutically acceptable composition having the device that is in the form of a transmucosal buccal tablet or buccal film. The pharmaceutically acceptable composition includes at least one buffering agent contained in said mucoadhesive layer for use in buffering the pH of ketamine or dextromethorphan, or both ketamine and dextromethorphan. Optionally, the pharmaceutically acceptable composition includes a hydrophobic polymer for coating said non-adhesive backing layer for controlling the erodibility of the layer Another embodiment of this invention includes a biomarker for identifying depressive disease in a patient comprising predicting responsiveness to treating a patient by administration to said patient of a pharmaceutically acceptable composition of ketamine, or dextromethorphan, or a combination of ketamine and dextromethorphan, and evaluating a change in alterations in acoustic vocal parameters comprising speech rate and voice frequency, and alterations in corticospinal excitability comprising resting motor threshold, in a patient at baseline prior to treatment and after treatment of said patient.

In another embodiment of this invention, a method of treating depression disease in a patient comprising administering to a patient an effective amount of a composition comprising an effective amount of dextromethorphan via the oral route of the patient for providing a rapid acting antidepressant effect for treating depression in the patient.

BRIEF DESCRIPTION OF THE DRAWINGS

FIG. 1 shows the results of the method of the present invention providing off-label use of a transbuccal ketamine formulation (i.e. a composition capable of delivering ketamine to a buccal cavity of a patient) for rapid acting treatment of depression disease.

DETAILED DESCRIPTION OF THE INVENTION

As used herein, the term "patient" means any member of the animal kingdom, including but not limited to human beings, and animals.

As used herein, the term "buccal" is defined as "of, relating to, adjacent to, or in the direction of the cheek" of the oral cavity of a patient. The term "buccal cavity" is defined as "the portion of the oral cavity of a patient bounded by the lips, cheeks, and gums". The term "buccal" is anatomically distinct from the "sublingual" region of the oral cavity. The term "sublingual" is defined as "below, or beneath the tongue".

As used herein, the term "mucosal" is defined as "a membrane for lining all body passages that communicate with the exterior, such as for example but not limited to the respiratory, genitourinary, oral, and rectal tracts of a patient's anatomy. The term "transmucosal" includes, for example, but not limited to administering a composition to the mucosal membrane of a patient including wherein the composition is capable of being held in contact with or in juxtaposition to mucosal membrane of a patient or applied to the mucosal membrane of a patient, and wherein said composition is permitted to be absorbed/adsorbed by or into the mucosal membrane of the patient.

As used herein, the term "effective amount" is defined as that amount of a substance, a drug, or a composition that is capable of bringing about a desired effect, such as for example, but not limited to, that amount of a substance, a drug, or a composition needed to treat a patient with depressive disease.

We test two strategies for achieving fast acting antidepressant effects with a much reduced side effect profile from existing options using an open-label, cross-over design: 1) transbuccal dosing of ketamine, and 2) oral administration of dextromethorphan (DM). In addition to performing standardized assessments using the Hamilton Depression Rating Scale (HAM-D), we evaluate two potential biomarkers of antidepressant efficacy to enable rapid future prediction of the onset of antidepressant actions: alterations in 1) voice parameters, and 2) corticospinal excitability. The methods and formulations and compositions of this invention improves therapeutic outcomes for individuals with depression.

The present invention shows that fast acting antidepressant effects can be achieved with tolerable side effects for translation into the general clinical population. In addition, predictive biomarkers of the onset of therapeutic actions are identified for quick and easy incorporation into standard practice settings. The present invention shows:

1. Demonstrate that transbuccal administration of ketamine produces fast acting antidepressant effects: To minimize some of the problematic side effects associated with intravenous administration of ketamine, recent investigations have attempted alternate routes of ketamine administration to elicit rapid antidepressant effects. Though the literature regarding oral ketamine dosing for depression remains mixed, off-label use of transbuccal ketamine in a day-hospital setting at Chestnut Ridge Center suggests that it can cause rapid antidepressant effects that last for approximately two weeks. The current proposal will validate the dose and route of administration, and systematically characterize the magnitude of the antidepressant effects and side effects, along with its time course.

2. Compare the efficacy of oral dextromethorphan (DM) as a fast acting antidepressant drug relative to ketamine: DM, which is most commonly used as a cough suppressant, shares many overlapping mechanisms of action with ketamine, but with a much more favorable safety profile. Therefore, we will determine whether similarly to ketamine, DM can produce rapid antidepressant actions. To facilitate comparisons between the two medications, Specific Aims 1 and 2 will be addressed using a cross-over design, with each patient serving as his or her own control.

3. Identify biomarkers that predict antidepressant efficacy: To complement HAM-D scores and provide additional validation of antidepressant efficacy, we will evaluate two biomarkers that have been previously shown to change with antidepressant therapy. In individuals who respond to antidepressant treatment, alterations in acoustic vocal parameters (eg. speech rate, voice frequency) and corticospinal excitability (e.g. resting motor threshold) have been reported. Since both of these measures can be easily and objectively quantified, we will evaluate the extent to which they predict responsiveness to treatment. Such tools will have value for identifying patients who are benefitting the most from treatment. This study ultimately contributes to the identification of fast acting antidepressant drugs that can be used safely and effectively by individuals suffering from depression.

This invention examines two strategies that are intended to evoke rapid antidepressant effects with more tolerable side effects than intravenous ketamine: 1) transbuccal ketamine, and 2) oral DM. Both medications are FDA-approved for other indications making them amenable for repurposing and quick translation into clinical settings. Ketamine: Ketamine is FDA-approved as an anesthetic agent. However, off-label use of the drug can elicit antidepressant effects within 24 hours of administration, with efficacy sustained for up to two weeks (i.e. rapid antidepressant effect). The rapid antidepressant effects of ketamine are thought to be initiated through its actions as an N-methyl-D-aspartate (NMDA) receptor antagonist, with the sustained effects of the drug resulting from synaptogesis and structural reorganization in the prefrontal cortex, a critical brain region that becomes compromised in depressions. Efforts thus far to overcome the side effect liabilities of ketamine have focused on: 1) elucidating the mechanism(s) of the ketamine effects in an effort to identify or develop new compounds with better tolerability (e.g. compounds that target mechanisms downstream from the NMDA receptor), and 2) utilizing alternate routes of administration and dosing to reduce the severity of the side effects. The first strategy has stimulated exciting new avenues of research in drug discovery which could benefit patients in the future. We have chosen to focus on the latter strategy which is likely to result in faster application into clinical practice. Preliminary data for ketamine. Based on published reports that oral dosing with ketamine could provide antidepressant effects in at least some patients, we have utilized this drug at Chestnut Ridge Center in treatment resistant patients, who have not responded to other antidepressant medications under conditions of standard off-label usage which is accepted in the profession. In these situations, patients are administered a 0.5 mg/kg dose of ketamine (which is a common dosage reported in the literature). In an effort to reduce side effects, liquid ketamine is placed on the tongue of the patients and they are instructed to hold it in their mouths for as long as possible. Thus, in contrast to standard oral dosing, where the drug is simply swallowed, the route of administration used in this method of this invention in our patients is described as transbuccal. These patients are generally seen daily for group therapy as part of our day-hospital program. Antidepressant effects, which are assessed by patient report and clinician observation, are generally seen within 24 hours and last for two weeks (FIG. 1), after which another dose of ketamine needs to be administered to maintain/re-establish therapeutic effects. No hallucinations, extreme sedation, euphoria, or other serious side effects have been reported under these conditions. The pilot study proposed herein will validate the efficacy of the transbuccal route of ketamine as a viable option for eliciting fast acting and sustained antidepressant effects, with a side effect profile suitable for use in out-patients. Dextromethorphan (DM): In contrast to the use of ketamine which is highly controlled, DM is available over-the-counter as a cough suppressant. It has been hypothesized to produce antidepressant actions based on overlapping mechanisms of action with ketamine, though peer-reviewed data have yet to be published. DM has moderate affinity for NMDA receptors, and is rapidly metabolized in the body to dextrorphan, a compound that produces robust NMDA antagonist actions similar to ketamine. In addition, dextromethophan and ketamine both have significant affinity for sigma receptors which elicits antidepressant/like actions in preclinical models and clinical trials, which may be of particular relevance for eliciting CNS structural adaptations that contribute to rapid and sustained therapeutic effects. Preliminary studies for DM: In preclinical studies, we have recently demonstrated that DM produces antidepressant like effects. Similar to ketamine and the tricyclic antidepressant drug imipramine, DM dose dependently reduces immobility time in the forced swim test, which is recognized as the most established animal model for predicting clinical antidepressant efficacy. These results suggest that similar to what has been hypothesized by a number of investigators, DM can be expected to produce antidepressant effects in humans. Biomarkers: Biomarkers are quantitative measurements that provide clinicians and researchers valuable insight into the diagnosis, treatment, and prognosis of pathological conditions. Since a significant challenge in treating individuals for depression is predicting who will respond/is responding to a particular pharmacotherapy (which can take weeks to develop with conventional medications), the identification of biomarkers for therapeutic responses to antidepressant treatment is invaluable. Though this is less of an issue with fast acting antidepressant drugs whose therapeutic effects are expected to appear within days of treatment, biomarker monitoring would still nonetheless be helpful for identifying individuals who are likely to benefit from a particular pharmacotherapy. Currently, the only objective, validated methods for determining response to antidepressant treatment are the use of standardized scales, such as the HAM-D. These generally should be administered by a health care professional and are thus not practical for daily monitoring. In the present proposal, we focus on two potential biomarkers (i.e. alterations in speech parameters and resting motor threshold) that would be relatively quick to administer and easy to incorporate into standard clinical practice. Speech parameters: Using commercially available software for detection of fundamental frequency and latency to respond, vocal prosody has been reported to have 79% accuracy in detecting depression. Based on earlier literature as well as observations in the clinic, the parameters that we are most interested in monitoring are speech rate and voice frequency variability because depressed individuals tend to speak slower and with a flattened intonation contour. These parameters can be easily measured from audio recordings of patients reading a standard reading passage. In addition, pause time between words and latency to respond to a standardized question will be quantified. Tremor and short-term frequency perturbation (vocal jitter) from a sustained phonation of "ah" will also be measured as they are known to increase in response to stress, a known risk factor for depression. Corticospinal excitability: An increased resting motor threshold in response to transcranial magnetic stimulation (TMS) has been reported in patients who are responding to antidepressant treatment, including electroconvulsive shock. This suggests that a decrease in corticospinal excitability may accompany rapid antidepressant effects that are produced by drugs, such as ketamine which has yet to be investigated. Innovation results from the identification of fast acting antidepressant drugs with a favorable side effect profile that is amenable to quick translation into the general clinical population. Moreover, validated biomarkers that are also amenable to rapid integration into normal clinical practice could assist in monitoring therapeutic outcomes in patients with depression. Approach an open-label, cross-over design will be used to assess the therapeutic efficacy of ketamine and DM in treatment resistant patients with major depression. Fast acting antidepressant effects with tolerable side effects can be achieved using transbuccal ketamine administration and/or oral DM methods and compositions of this invention. Moreover, we expect that the onset of antidepressant effects will be preceded by alterations in vocal prosody and resting motor threshold responses. We discuss the research design including but not limited to such issues as: probability of group assignment, potential for subject to be randomized to placebo group, use of control subjects, etc.

This is a pilot study to test the effect of Ketamine and Dextromethorphan on mood in patients with treatment resistant depression. Study will be conducted at Chestnut Ridge Center, Day Hospital. We plan to recruit 10 patients in this pilot study which will be a cross over study in which patient will act as their own control. Patients recruited will have an initial clinical interview and will be assessed for psychiatric psychopathology and medication trials that they have had. All patients will receive a Personality Assessment Inventory (PAI) All patients in study will have initial screen which is the HAM-D prior to administration of any medication. Patients will then receive a one-time dose of 0.5 mg/kg of oral ketamine at Chestnut Ridge Center which will be supervised and monitored by nursing staff. Patients will be asked to keep in their mouth as long as they can to enhance oral absorption of the medication. They will be requested to come the morning of receiving medications empty stomach. Patients will then continue with their routine group therapy at the Day Hospital at Chestnut Ridge Center and during this time they will also be closely monitored for any adverse effects of the medications. Patients will be assessed 5 days a week, while they attend group therapy at the day hospital. During this assessment will assess for mood through repeat HAM-D and side effects from the medication. At 2 weeks, will repeat same one time dosage of 0.5 mg/kg of oral ketamine and continue to monitor for side effects and mood like done previously. At the end of one month, patients will have a cross over to dextromethorphan. Patients will be getting one time dose of 2.7 mg/kg dextromethorphan. Patients will then continue with their routine group therapy at the Day Hospital at Chestnut Ridge Center and during this time they will also be closely monitored for any adverse effects of the medications. Patients will be assessed 5 days a week, while they attend group therapy at the day hospital. During this assessment will assess for mood through repeat HAM-D and side effects from the medication. Primary outcome measures:—HAM-D Secondary outcome measures:—TMS—Speech pathology assessment for rate and range of speech.

Specify inclusion criteria:
    Age 19 years and older.—Patients with moderate to severe depression.

Specify exclusion criteria:
    Patients with known liver disease.—Patients with life threatening medical problems,—Currently medically unstable patients.—Pregnant women—Infants and children—Patients who lack medical decision making capacity.

Patient who would require medication adjustment during time in the study.

Patients will be monitored closely on a regular basis, 5 days a week in the Day Hospital and Chestnut Ridge Center. Patient will be closely monitored from symptoms immediately after administration of drug (ketamine/dextromethorphan). Patients will be seen 5 days a week in medical rounds by staff psychiatrist and nursing staff and will be assessed for any side effects of medications. In case of any immediate life threatening side effects patients that may arise patients will be sent to Ruby Memorial Hospital for further evaluation and treatment. These patients will not be permitted to continue with study.

Patients who are enrolled in this study will have met the DSN-IV diagnostic criteria for major depression and will be considered treatment resistant, making them well suited candidates for innovative treatment options. They will be instructed to arrive on an empty stomach the mornings they receive medication (i.e. no food after 9:00 p.m. the previous night). In addition to receiving study medications, they will be expected to participate in the day-hospital treatment program at Chestnut Ridge Center which includes daily therapy sessions (which represents standard care for these patients). Baseline measurements: Prior to initiating drug therapy with ketamine, baseline assessments will be performed for the following: 1) HAM-D, 2) standard reading passage (for the measurement of voice parameters), and 3) TMS. The HAM-D will be performed by the M.D./Ph.D. student. It was chosen over other depression scales because it has been effective in detecting antidepressant effects of both ketamine and sigma receptor agonists. For the measurement of voice parameters, study participants will be recorded reading a standard reading passage (Rainbow Passage), producing a sustained vocalization ("ah"), and responding to a standardized question. The digital audio recordings will be analyzed using a Computerized Speech Lab (CSL, Model 4400; KayPentax, Lincoln Park, NJ) system. The mean speech rate (syllables per second), response latency, and percent pause time will be determined using KayPentax Motor Speech Profile (MSP Model 5141) software. The mean vocal fundamental frequency, tremor rate, frequency range, and frequency perturbation (vocal jitter) will be determined using KayPentax Multi-Dimensional Voice Profile (MDVP Model 5105) software. The determination of corticospinal excitability will be made using single-pulse TMS of the primary motor cortex. Responses to TMS, motor evoked potentials, will be obtained from surface electromyogram of the first dorsal interosseous muscle of the dominant hand. Resting motor threshold will be determined for each subject as the lowest TMS amplitude that causes motor evoked potentials larger than 50 µV in 50% of trials when the arm is at rest. It should be emphasized that the TMS parameters used in this portion of the study will be well below those used to elicit antidepressant effects on their own. Ketamine trial: The first treatment arm will evaluate ketamine. Following baseline measurements, the subjects will be taken to a quiet, non-exam room for the next hour, where they will be given a one time dose of 0.5 mg/kg of liquid ketamine and instructed by the nursing staff to hold it in their mouths for as long as possible to enhance absorption of the medication; they will be allowed to relax and will be unobtrusively observed for potential side effects during this time. Subjects will then continue their routine group therapy as part of the day-hospital program at Chestnut Ridge and during which time they will continue to be monitored by health care staff for adverse effects of the medication (e.g. extreme sedation and hallucinations which have been problematic after intravenous dosing of ketamine; suicidal ideation after SSRIs). Subjects will be assessed five days a week as described for the baseline measurements using the HAM-D, voice recordings, and IMS, before they attend group therapy at the day-hospital. Since earlier observations and reports indicate that the ketamine effects last for approximately two weeks, at the start of the third week, the subjects will receive another one-time dose of 0.5 mg/kg liquid ketamine in order to establish reproducibility of the response for each subject. The monitoring and data collection will occur as described for the initial two weeks of treatment. At the end of one month (the second two-week period with ketamine), the subjects will cross-over to testing with DM. DM trial: The second treatment arm will evaluate DM. For the purposes of this pilot study, all of the subjects will initially receive ketamine since much more is known about the use of this drug as a fast acting antidepressant, providing a credible point of reference for comparisons to DM, which we hope to be the first to report as an antidepressant drug. For the initial evaluation, we will test a single oral dose of DM, 2.7 mg/kg, which was selected because it roughly matches the subjective effects produced by ketamine at its test dose of 0.5 mg/kg. Though this dose of DM is slightly higher than its FDA-recommended dose for cough suppression 120 mg/day, we do not anticipate problems with serious side effects because it is not unusual for individuals to take more than the recommended dose, with reports of abuse involving dosages measured in grams. Similar to the ketamine arm of the trial, subjects will be closely monitored for side effects, and evaluated using the HAM-D, standard reading passage, and TMS in association with their daily group therapy sessions five days a week as part of the day-hospital program at Chestnut Ridge. Three possible outcomes are anticipated: 1) DM produces effects comparable to ketamine, 2) DM produces transient therapeutic effects, or 3) DM has no significant therapeutic effects. If therapeutic effects are observed during the initial two-week evaluation of DM, then at the start of the third week, a second one-time DM dose of 2.7 mg/kg will be administered to evaluate the reproducibility of the effect. If transient or no therapeutic effects are observed during the initial two-week trial with DM, then the dose of DM administered at the start of the third week will be doubled to 5.4 mg/kg. Assessments will be performed as described for the previous drug exposures.

Study participants are treatment resistant and not responding to currently available antidepressant drugs. Therefore, they may benefit from improved mood with the proposed study medication, with the effects anticipated to occur much more rapidly than convention antidepressant drugs. Subjects will also benefit from participation in group therapy as part of the day hospital program at Chestnut Ridge Center.

The potential benefits of this research to society and the scientific/medical community is that fast acting antidepressant treatments that are amenable to use in the general population may be identified. Also, simple to use biomarkers to predict antidepressant efficacy may also be identified which can be readily implemented in standard clinical settings. Current antidepressant drugs take several weeks before therapeutic benefits are achieved, and about 30% of individuals still do not respond. Heretofore, fast acting antidepressant drugs that can be used in the general population are unavailable. The identification of such a composition and methods, as set forth in this invention transforms the treatment of depression in patients.

Treatment resistant depression is a leading cause of morbidity and mortality in the world. Many patients have tried multiple medications with minimal response. Ketamine and dextromethorphan are both medications that are well known with side effect profiles being well studied and monitored. Use of ketamine and dextromethorphan as antidepressants opens up a new avenue of hope in patients who have been battling with depression that have not responded to conventional treatment.

HUMAN SUBJECTS

Protection of Human Subjects

1. Risk to Human Subjects
   a. Human Subjects Involvement, Characteristics, and Design
   We recruit 10 individuals, age 18 years and older, with treatment resistant depression as subjects for this study. Exclusion criteria include individuals with substance abuse, cardiac disease or arrhythmia; individuals who require adjustments of other medications during the time course of the study; women who are pregnant or nursing; infants, children under 18, and others who are unable to provide their own consent. Existing medications that the subjects are taking will not serve as exclusion criteria unless they have known drug-drug interactions with the study medications, or if the doses will be significantly altered during the course of the study; since the patients are treatment resistant (i.e. failed to respond to at least two conventional medication options), as long as their current medications remain constant throughout the study and do not interact with the study drugs, they should not affect the outcome. All aspects of the study will be performed at the Chestnut Ridge Center and the WVU Health Sciences Center by trained personnel. The subjects will be administered drugs that are anticipated to produce rapid antidepressant effects in an open label cross over design, and participate in group therapy sessions. They will also be administered the HAM-D scale, recordings of them reading a standard reading passage (i.e. Rainbow Passage[1]) will be made, along with TMS measurements. Subjects will have their corticospinal excitability measured using TMS. TMS is a noninvasive, pain free way to stimulate the human cortex. Single-pulse TMS is considered to have no significant safety risks.[2] The text of the Rainbow Passage is as follows: "When the sunlight strikes raindrops in the air, they act like a prism and form a rainbow. The rainbow is a division of white light into many beautiful colors. These take the shape of a long round arch, with its path high above, and its two ends apparently beyond the horizon. There is, according to legend, a boiling pot of gold at one end. People look, but no one ever finds it. When a man looks for something beyond his reach, his friends say he is looking for the pot of gold at the end of the rainbow." Each patient will receive ketamine in the first treatment arm and then dextromethorphan/ quinidine in the second treatment arm. This set up allows for easy comparisons between the two treatments, as the first one is a known fast acting antidepressant that will prime the patients to evaluate any therapeutic benefits of a novel, potentially fast acting, antidepressant.

b. Sources of Materials

The assessment of therapeutic response will be measured using the HAM-D scale and clinical observations. Side effects (if any, e.g. perceptual disturbances, confusion, elevated blood pressure, elevated heart rate, sedation, and euphoria) will also be noted. All collected data will be de-identified and assigned a subject code for analysis. The data will be kept in locked areas which can be accessed only by study personnel.

c. Potential Risks

The risks to the subjects for participation in the study are low, relative to the risks associated with their depression remaining untreated due to unresponsiveness to existing antidepressant drugs (treatment resistant). Both study medications, ketamine and dextromethorphan/quinidine, are FDA-approved. Earlier reported side effects with intravenous administration of subanesthetic doses of ketamine include: perceptual disturbances, confusion, elevated blood pressure, sedation, and a short lived "high". No side effects (except for a transient, mild headache and slight dizziness in one patient each soon after administration) were observed in the patients in the preliminary data (oral mucosa absorption of ketamine). The efficacy of ketamine as a fast acting antidepressant drug has been reported in the scientific literature using intravenous administration; the proposed administration route is expected to reduce many of the side effects associated with the intravenous route of administration, with the dose chosen for this study previously showing efficacy with off-label use at the study site. Dextromethorphan/quinidine is available for the treatment of pseudobulbar affect and is considered a safer alternative to ketamine. The two doses of dextromethorphan/quindine proposed for use meets the FDA- and EMA-approved oral doses for the treatment of pseudobulbar affect, and were selected to provide initial insights into its potential antidepressant efficacy. We do not anticipate serious side effects with these doses. Moreover, the drugs will be administered to study participants one-hour prior to beginning their first day of group therapy at Chestnut Ridge Center, where they will be under the observation of health care professionals. They will return for daily group therapy sessions for five days each week, providing ample opportunity for them to be directly observed by health care professionals for untoward side effects. In the unlikely event that they require medical attention when not on site, they will be provided cards containing the contact information for the P.I.s and advised to have the emergency room or urgent care provider notify them.

2. Adequacy of Protection Against Risks a. Recruitment and Informed Consent

Subjects will be recruited through the Chestnut Ridge Center, or through local advertisements if needed. Personnel affiliated with the study will obtain informed consent from all study participants. Informed consent involves an explanation of possible risks and benefits of participating in the study, as well as rights afforded to participants during the study. Specifically, informed consent will contain the study procedure, duration, possible risks and benefits, confidentiality, researcher contact information, and other pertinent information (e.g., the right to withdraw consent at any time) so that participants can make an informed decision before participating. Personnel will also be available to answer any questions the participant may have about the study, or their rights and responsibilities as a research participant. All forms and study information that can be linked to a specific individual will kept in a locked file cabinet at Chestnut Ridge Center that can be accessed only by study personnel. Confidentiality will further be maintained through the use of de-identified data for analysis and reporting. Exclusion criteria include individuals with substance abuse, cardiac disease or arrhythmia; individuals who require adjustments of other medications during the time course of the study; women who are pregnant or nursing; infants, children under 18, and others who are unable to provide their own consent.

b. Protections Against Risk

Although the potential risks of participation in these studies are anticipated to be minimal, measures will be taken to further protect against risk. Children 18 years of age and older will be allowed to participate as they are capable of providing their own informed consent and thus will receive the same protections against risk as adults. Patients will undergo group therapy at Chestnut Ridge Center five days each week of the study, including the days that they receive study medications. If side effects are observed, they will be expeditiously treated on-site. If treatment in an emergency room or urgent care center is needed when outside of the study environment, the subjects will have cards containing the contact information for the P.I.s and advised to have the care provider notify them. All adverse events will be reported to an internal data safety and monitoring board in the department and the IRB for review. Furthermore, confidentiality will be carefully guarded at all stages of participation. At no time will participants' names be associated with any data provided. All materials will be stored separately in locked filing cabinets that are only accessible to the research team. These measures have been used successfully by the team members in the past, and we expect that they will continue to be effective at minimizing potential risks to participants.

3. Benefits of the Research to Human Subjects and Others

Study participants are treatment resistant and not responding to currently available antidepressant drugs. Therefore, they may benefit from improved mood with the proposed study medication, with the effects anticipated to occur much more rapidly than convention antidepressant drugs. Subjects will also benefit from participation in group therapy as part of the day hospital program at Chestnut Ridge Center. The benefits of this invention to society and the scientific/medical community is that fast acting antidepressant treatments of this invention are amenable to use in the general population. Also, simple to use biomarkers to predict antidepressant efficacy may also be identified which can be implemented in standard clinical settings.

4. Importance of the Knowledge to be Gained

Current antidepressant drugs take several weeks before therapeutic benefits are achieved, and about 30% of individuals still do not respond.

5. Data and Safety Monitoring Plan

The compositions of this invention are administered to participants one-hour prior to beginning group therapy at Chestnut Ridge Center, where they will be under continuous observation by health care professionals. They will return for daily group therapy sessions for five days each week, for the next two weeks, providing ample opportunity for them to be directly observed by health care professionals for untoward side effects. In the unlikely event that subjects require medical attention when not on site, they will be provided cards containing the contact information for the P.I.s and advised to have the emergency room or urgent care provider notify them. Adverse events related to participation in the study will be reported to an internal data safety and monitoring board in the Department of Behavioral Medicine and Psychiatry and IRB for review.

In one embodiment of the present invention, a method is provided of treating depression disease in a patient comprising administering to a mucosal membrane of a patient an effective amount of a composition comprising an effective amount of ketamine, wherein said mucosal administration of said composition allows for the transmucosal absorption of the composition into the patient's blood stream thereby eliminating the digestive tract of said patient for providing a rapid acting antidepressant effect for treating depression in the patient. This method includes including administering said composition to said mucosal membrane of said patient over a time period from one millisecond to ten minutes, and preferably over a time period that is from one second to three minutes. This method includes providing said composition contained within a dosage form capable of being administered to the mucosa of said patient or to the mucosal membrane of said patient. Preferably this method includes providing wherein said dosage form is a liquid, gel, powder. More preferably, this method includes providing said dosage form that is in the form of a pharmaceutically acceptable troche, film, capsule, tablet, particle, solution, suspension, lollipop, lozenge, emulsion, spray, or aerosol. This method includes providing an effective amount of said ketamine that is 0.5 mg per kilogram of a patient's body mass. The method includes administering said composition to said mucosal membrane that is in an oral cavity of said patient. Preferably, the method includes administering said composition to a buccal cavity of said oral cavity of said patient. This method includes, for example, wherein said depression is selected from the group of unipolar depression disease, bipolar depression disease, and depression treatment resistant disease. An optional embodiment of this method includes wherein said administration of said ketamine is followed by administering to said patient an effective amount of a composition comprising an effective amount of dextromethorphan, and preferably administering said composition comprising dextromethorphan in within a clinically effective time period from the administration of said composition comprising ketamine, and more preferably administering said composition comprising dextromethorphan within ninety days from the administration of said composition comprising ketamine.

In another embodiment of this invention, a pharmaceutically acceptable composition is provided comprising an effective amount of ketamine, wherein said ketamine is distributed within a pharmaceutically acceptable vehicle, wherein said vehicle is capable of being placed in contact with a mucosal membrane of a patient. The pharmaceutically acceptable composition and said vehicle are capable of delivery to an oral cavity of said patient. Preferably, said composition and said vehicle are capable of delivery to a buccal cavity of the oral cavity of said patient. The pharmaceutically acceptable composition includes wherein said composition has a dosage form that is a liquid, gel, or powder. More preferably, the pharmaceutically acceptable composition of this invention is a dosage form of a pharmaceutically acceptable troche, film, capsule, tablet, particle, solution, suspension, lollipop, lozenge, emulsion, spray, or aerosol. Most preferably, the pharmaceutically acceptable composition of this invention includes wherein said effective amount of said ketamine is 0.5 mg per kilogram of a patient's body mass.

Another embodiment of this invention provides a pharmaceutically acceptable composition comprising an effective amount of ketamine, wherein said ketamine is distributed within a pharmaceutically acceptable vehicle, wherein said vehicle is capable of being placed in contact with a mucosal membrane of a patient, and wherein the pharmaceutically acceptable vehicle is a device having a mucoadhesive layer containing said ketamine buffered to a pH of between about 4.0 and 7.0, and a non-adhesive backing layer buffered to a pH of between 4.0 and 6.0 wherein the pH of the mucoadhesive layer and the non-adhesive backing layer are different wherein the mucoadhesive layer and the non-adhesive backing layer comprise different combinations of polymers but each layer comprises at least one water-erodible polymer selected from the group of cellulosic polymers, olefinic polymers, polyethers, and polyalcohols, wherein following transmucosal administration excessive exposure to ketamine is avoided. Most preferably, the amount of ketamine contained within said mucoadhesive layer is 0.5 mg per kilogram of a patient's body mass. Preferably, the water-erodible polymer is selected from the group consisting of polyacrylic acid, sodium carboxymethylcellulose, hydroxyethyl cellulose, hydroxyethylmethyl cellulose, hydroxyethyl cellulose, hydroxypropyl cellulose, polyvinyl alcohol, polyethylene glycol, polyethylene oxide, and ethylene oxide-propylene oxide co-polymers. The device may be in the form of a transmucosal buccal tablet, buccal film, and the like. Those persons skilled in the art understand that any number of buffering agents may be included in the mucoadhesive layer with said ketamine for use in buffering the pH of ketamine, wherein such buffering agents include, but are not limited to for example, phosphates, phosphates monobasic, phosphates dibasic, phosphates tribasic, bicarbonates, acetates, and combinations thereof. The non-adhesive backing layer may be further modified to control the erodibility of the layer by coating the non-adhesive backing layer with a hydrophobic polymer such as for example but not limited to ethyl cellulose, cellulose acetate phthalate, and hydroxyl propyl methyl cellulose phthalate, provided that the non-adhesive backing layer erodes in a moist environment of the oral cavity. Dissolution characteristics of the mucoadhesive layer and the bioavailability of ketamine may be adjusted accordingly depending upon the water-erodible polymer employed in the formulation of the device.

Another embodiment of this invention provides a biomarker for identifying a depression disease in a patient. The biomarker of this invention comprises predicting responsiveness to treating a patient by administration to said patient a pharmaceutically acceptable composition of ketamine, or dextromethorphan, or a combination of ketamine and dextromethorphan, and evaluating a change in alterations in acoustic vocal parameters comprising speech rate and voice frequency, and alterations in corticospinal excitability comprising resting motor threshold, in a patient at baseline prior to treatment and after treatment of said patient.

In yet another embodiment of this invention, a method of treating depression disease in a patient is provided comprising administering orally or to a mucosal membrane of a patient an effective amount of a composition comprising an effective amount of dextromethorphan, wherein said mucosal administration of said composition allows for the transmucosal absorption of the composition into the patient's blood stream thereby eliminating the digestive tract of said patient for providing a rapid acting antidepressant effect for treating depression in the patient. This method includes administering said composition to said mucosal membrane of said patient over a time period from one millisecond to ten minutes, and preferably over a time period that is from one second to three minutes. This method includes wherein said composition is contained within a dosage form capable of being administered to the mucosa of said patient or to the mucosal membrane of said patient. Preferably, this method includes providing said dosage form that is a liquid, gel, powder. More preferably, this method includes providing said dosage form that is in the form of a pharmaceutically acceptable troche, film, capsule, tablet, particle, solution, suspension, lollipop, lozenge, emulsion, spray, or aerosol. This method includes administering said composition to said mucosal membrane that is in an oral cavity of said patient. Preferably, this method includes administering said composition to a buccal cavity of said oral cavity of said patient. This method includes wherein the depression is selected from the group of unipolar depression disease, bipolar depression disease, and depression treatment resistant disease. This method optionally includes wherein said oral administration includes swallowing said composition comprising dextromethorphan.

Another embodiment of this invention provides a pharmaceutically acceptable composition comprising an effective amount of dextromethorphan, wherein said dextromethorphan is distributed within a pharmaceutically acceptable vehicle, wherein said vehicle is capable of being placed in contact with a mucosal membrane of a patient. The pharmaceutically acceptable composition includes wherein said composition and said vehicle are capable of delivery to an oral cavity of said patient, and preferably wherein said composition and said vehicle are capable of delivery to a buccal cavity of the oral cavity of said patient. The pharmaceutically acceptable composition of includes wherein said composition has a dosage form that is a liquid, gel, or powder, and preferably the pharmaceutically acceptable composition is a dosage form of a pharmaceutically acceptable troche, film, capsule, tablet, particle, solution, suspension, lollipop, lozenge, emulsion, spray, or aerosol. The pharmaceutically acceptable composition includes wherein said effective amount of said dextromethorphan is from 0.5 mg to 2000.0 mg per dosage form.

Another embodiment of this invention provides a pharmaceutically acceptable composition comprising an effective amount of dextromethorphan, wherein said dextromethorphan is distributed within a pharmaceutically acceptable vehicle, wherein said vehicle is capable of being placed in contact with a mucosal membrane of a patient, and wherein the pharmaceutically acceptable vehicle is a device having a mucoadhesive layer containing said dextromethorphan buffered to a pH of between about 4.0 and 7.0, and a non-adhesive backing layer buffered to a pH of between 4.0 and 6.0 wherein the pH of the mucoadhesive layer and the non-adhesive backing layer are different and wherein the mucoadhesive layer and the non-adhesive backing layer comprise different combinations of polymers but each layer comprises at least one water-erodible polymer selected from the group of cellulosic polymers, olefinic polymers, polyethers, and polyalcohols, wherein following transmucosal administration excessive exposure to dextromethorphan is avoided. Most preferably, the amount of dextromethorphan contained within said mucoadhesive layer is from 0.5 mg to 2000.0 mg per dosage form. Preferably, the water-erodible polymer is selected from the group consisting of polyacrylic acid, sodium carboxymethylcellulose, hydroxyethyl cellulose, hydroxyethylmethyl cellulose, hydroxyethyl cellulose, hydroxypropyl cellulose, polyvinyl alcohol, polyethylene glycol, polyethylene oxide, and ethylene oxide-propylene oxide co-polymers. The device may be in the form of a transmucosal buccal tablet, buccal film, and the like. Those persons skilled in the art understand that any number of buffering agents may be included in the mucoadhesive layer with said dextromethorphan for use in buffering the pH of dextromethorphan, wherein such buffering agents include, but are not limited to for example, phosphates, phosphates monobasic, phosphates dibasic, phosphates tribasic, bicarbonates, acetates, and combinations thereof. The non-adhesive backing layer may be further modified to control the erodibility of the layer by coating the non-adhesive backing layer with a hydrophobic polymer such as for example but not limited to ethyl cellulose, cellulose acetate phthalate, and hydroxyl propyl methyl cellulose phthalate, provided that the non-adhesive backing layer erodes in a moist environment of the oral cavity. Dissolution characteristics of the mucoadhesive layer and the bioavailability of dextromethorphan may be adjusted accordingly depending upon the water-erodible polymer employed in the formulation of the device.

In another embodiment of this invention, a method is provided of treating depression disease in a patient comprising administering to a patient an effective amount of a composition comprising an effective amount of dextromethorphan via the oral route of said patient for providing a rapid acting antidepressant effect for treating depression in the patient.

It will be appreciated that the method and rapid acting pharmaceutically acceptable compositions of this invention are effective treatment of depression in treatment resistant patients. These inventions change the world of antidepressant pharmacotherapy as they grant to these patients antidepressant therapy within 24 hours of treatment and in turn decrease the morbidity associated with depressive illness.

REFERENCES

[1] Fairbanks G. The rainbow passage. In: *Voice and Articulation Drillbook* (2nd ed). New York: Harper & Row; 1960; 127.

[2] Groppa S, Oliviero A, Eisen A, Quartarone A, Cohen L G, Mall V, Kaelin-Lang A, Mima T, Rossi S, Thickbroom G W, Rossini P M, Ziemann U, Valls-Solé J, Siebner H R. A practical guide to diagnostic transcranial magnetic stimulation: Report of an IFCN committee. Clin Neurophysiol. 2012 May; 123(5):858-882.

Jick H, Kaye J A, Jick S S. Antidepressants and risk of suicidal behaviors. JAMA 2004; 292 (3): 338-43.

Rot M A, Collins K A, Murrough J W. Safety and efficacy of repeated low dose intravenous ketamine for treatment-resistant depression. Biol Psychiatry 2010; 67: 139-145.

Papp M, Moryl E. Antidepressant activity of non-competitive NMDA receptor antagonists in a chronic mild stress model of depression. EUR J Pharmacol. 1994; 263 (1-2): 1-7.

Zarate C A, Singh J B, Carlson P J. A randomized trial of an N-methyl-D-aspartate antagonist in treatment-resistant major depression. Arch Gen Psychiatry 2006; 63 (8) 856-864.

What is claimed is:

1. A pharmaceutically acceptable composition comprising:

an effective amount of ketamine or dextromethorphan, or both ketamine and dextromethorphan, wherein said ketamine or said dextromethorphan, or both are distributed within a pharmaceutically acceptable vehicle, wherein said vehicle is capable of being placed in contact with a mucosal membrane of a patient, and wherein said pharmaceutically acceptable vehicle is a device having a mucoadhesive layer containing said ketamine buffered to a pH of between about 4.0 and 7.0, and a non-adhesive backing layer buffered to a pH of between 4.0 and 6.0 wherein the pH of said mucoadhesive layer and said pH of said non-adhesive backing layer are different, wherein said mucoadhesive layer and said non-adhesive backing layer comprise different combinations of polymers but each of said mucoadhesive layer and said non-adhesive backing layer comprise at least one water-erodible polymer wherein said water-erodible polymer is one selected from the group consisting of a cellulosic polymer, an olefinic polymer, a polyether, and a polyalcohol.

2. The pharmaceutically acceptable composition of claim 1 wherein said composition and said vehicle are capable of delivery to a mucosal membrane of a genitourinary tract, an oral tract, or rectal tract of said patient.

3. The pharmaceutically acceptable composition of claim 1 wherein said composition and said vehicle are capable of delivery to an oral cavity of said patient.

4. The pharmaceutically acceptable composition of claim 1 including wherein said composition has a dosage form that is a liquid, gel, or powder.

5. The pharmaceutically acceptable composition of claim 1 including wherein said effective amount of said dextromethorphan is 0.5 mg to 2000.0 mg per dosage form, and wherein said effective amount of said ketamine is approximately 0.5 mg per kilogram of a patient's body mass per dosage form.

6. A pharmaceutically acceptable composition comprising:

an effective amount of ketamine or dextromethorphan, or both ketamine and dextromethorphan, wherein said ketamine or said dextromethorphan, or both are distributed within a pharmaceutically acceptable vehicle, wherein said vehicle is capable of being placed in contact with a mucosal membrane of a patient, and wherein said pharmaceutically acceptable vehicle is a device having a mucoadhesive layer containing said ketamine buffered to a pH of between about 4.0 and 7.0, and a non-adhesive backing layer buffered to a pH of between 4.0 and 6.0 wherein the pH of said mucoadhesive layer and said pH of said non-adhesive backing layer are different, wherein said mucoadhesive layer and said non-adhesive backing layer comprise different combinations of polymers but each of said mucoadhesive layer and said non-adhesive backing layer comprise at least one water-erodible polymer wherein said water-erodible polymer is at least one selected from the group consisting of a sodium carboxymethylcellulose, a hydroxyethyl cellulose, a hydroxyethylmethyl cellulose, a hydroxyethyl cellulose, a hydroxypropyl cellulose, a polyvinyl alcohol, a polyethylene glycol, a polyethylene oxide, and an ethylene oxide-propylene oxide co-polymer.

7. The pharmaceutically acceptable composition of claim 1 wherein said device is in the form of a transmucosal buccal tablet or buccal film.

8. The pharmaceutically acceptable composition of claim 1 including at least one buffering agent contained in said mucoadhesive layer for use in buffering the pH of ketamine or dextromethorphan, or both ketamine and dextromethorphan.

9. The pharmaceutically acceptable composition of claim 8 wherein said buffering agent is one selected from the group consisting of phosphates, phosphates monobasic, phosphates dibasic, phosphates tribasic, bicarbonates, acetates, and combinations thereof.

10. The pharmaceutically acceptable composition of claim 1 including a hydrophobic polymer for coating said non-adhesive backing layer for controlling the erodibility of said non-adhesive backing layer.

* * * * *